US012667362B2

(12) United States Patent
Wang et al.

(10) Patent No.: US 12,667,362 B2
(45) Date of Patent: Jun. 30, 2026

(54) EMBOLIC DEVICE DELIVERY SYSTEM

(71) Applicant: Covidien LP, Mansfield, MA (US)

(72) Inventors: Yihan Wang, Shanghai (CN); Yuqiang Wang, Shanghai (CN); Yunguo Qin, Shanghai (CN); Junmin Guo, Shanghai (CN); Shengfeng Shi, Shanghai (CN)

(73) Assignee: Covidien LP, Mansfield, MA (US)

( * ) Notice: Subject to any disclaimer, the term of this patent is extended or adjusted under 35 U.S.C. 154(b) by 797 days.

(21) Appl. No.: 17/627,783

(22) PCT Filed: Jul. 19, 2019

(86) PCT No.: PCT/CN2019/096827
§ 371 (c)(1),
(2) Date: Jan. 17, 2022

(87) PCT Pub. No.: WO2021/012097
PCT Pub. Date: Jan. 28, 2021

(65) Prior Publication Data
US 2022/0313269 A1 Oct. 6, 2022

(51) Int. Cl.
*A61B 17/12* (2006.01)

(52) U.S. Cl.
CPC .... *A61B 17/12109* (2013.01); *A61B 17/1214* (2013.01); *A61B 2017/12054* (2013.01)

(58) Field of Classification Search
CPC .......... A61B 17/12109; A61B 17/1214; A61B 2017/12054; A61B 17/12145;
(Continued)

(56) References Cited

U.S. PATENT DOCUMENTS

| 5,725,546 A | 3/1998 | Samson |
| 6,113,622 A | 9/2000 | Hieshima |
| (Continued) | | |

FOREIGN PATENT DOCUMENTS

| CN | 102125451 A | 7/2011 |
| CN | 103989499 A | 8/2014 |
| (Continued) | | |

OTHER PUBLICATIONS

Extended European Search Report from counterpart European Application No. 19938340.7 dated Mar. 24, 2023, 10 pp.
(Continued)

*Primary Examiner* — Kathleen S Holwerda
*Assistant Examiner* — James R. Mcginnity
(74) *Attorney, Agent, or Firm* — Shumaker & Sieffert, P.A.

(57) ABSTRACT

A distal portion (16) of an elongated body (12) is configured to mate with a distal portion (20) of an interface member (18) mechanically connected to an embolization device (22). The embolization device (22) is additionally attached to the elongated body (12). The elongated body distal portion (16) and the interface member proximal portion (19) may collectively define a protrusion and a recess configured to receive the protrusion to provide the mating. The elongated body (12), interface member (18), and embolization device (22) may be configured for delivery to a vasculature target site, and manipulation of the deployed embolization device (22) may be facilitated by the mating between the elongated body (12) and the interface member (18).

19 Claims, 11 Drawing Sheets

(58) Field of Classification Search
CPC ... A61B 2017/00477; A61F 2002/9511; A61F 2002/9665; A61F 2002/9505
See application file for complete search history.

(56) References Cited

U.S. PATENT DOCUMENTS

| | | | |
|---|---|---|---|
| 7,942,894 B2 | 5/2011 | West | |
| 8,328,860 B2 | 12/2012 | Strauss et al. | |
| 8,414,634 B2 | 4/2013 | Sekido et al. | |
| 8,500,773 B2 | 8/2013 | Nardone et al. | |
| 8,864,790 B2* | 10/2014 | Strauss | A61F 2/01 606/200 |
| 9,119,948 B2 | 9/2015 | Lee et al. | |
| 9,149,278 B2 | 10/2015 | Slazas et al. | |
| 9,579,104 B2 | 2/2017 | Beckham et al. | |
| 9,795,389 B2 | 10/2017 | Elliott | |
| 10,034,670 B2 | 7/2018 | Elgård et al. | |
| 10,238,396 B2 | 3/2019 | Tassoni et al. | |
| 12,114,863 B2* | 10/2024 | Bowman | A61F 6/22 |
| 2002/0188311 A1 | 12/2002 | Ferrera et al. | |
| 2005/0149108 A1 | 7/2005 | Cox | |
| 2006/0025801 A1* | 2/2006 | Lulo | A61B 17/12022 606/200 |
| 2006/0229702 A1* | 10/2006 | Agnew | A61F 2/966 623/1.11 |
| 2007/0112375 A1 | 5/2007 | Aganon et al. | |
| 2007/0179507 A1* | 8/2007 | Shah | A61B 17/50 606/113 |
| 2008/0306504 A1* | 12/2008 | Win | A61B 17/1214 606/191 |
| 2010/0042133 A1 | 2/2010 | Ramzipoor et al. | |
| 2012/0265237 A1 | 10/2012 | Evert | |
| 2014/0058435 A1 | 2/2014 | Jones et al. | |
| 2014/0207175 A1 | 7/2014 | Aggerholm | |
| 2014/0236127 A1* | 8/2014 | Lee | A61B 17/1214 606/191 |
| 2015/0216688 A1 | 8/2015 | Landsman et al. | |
| 2015/0327868 A1 | 11/2015 | Islak et al. | |
| 2015/0327976 A1 | 11/2015 | Divino et al. | |
| 2016/0228123 A1 | 8/2016 | Anderson et al. | |
| 2016/0228125 A1 | 8/2016 | Pederson, Jr. et al. | |
| 2016/0302794 A1 | 10/2016 | Torp et al. | |
| 2017/0007266 A1 | 1/2017 | Smith et al. | |
| 2017/0095258 A1 | 4/2017 | Tassoni et al. | |
| 2017/0105739 A1 | 4/2017 | Dias et al. | |
| 2017/0367704 A1 | 12/2017 | Rhee et al. | |
| 2017/0367709 A1 | 12/2017 | Divino et al. | |
| 2018/0256171 A1* | 9/2018 | Chow | A61B 17/12159 |
| 2018/0263629 A1 | 9/2018 | Murphy et al. | |
| 2019/0254678 A1* | 8/2019 | Dinges | A61B 17/12022 |
| 2020/0069313 A1* | 3/2020 | Xu | A61B 17/1214 |
| 2021/0068998 A1* | 3/2021 | Li | A61B 17/12145 |

FOREIGN PATENT DOCUMENTS

| | | |
|---|---|---|
| CN | 1652726 A | 8/2015 |
| DE | 19547617 | 9/1997 |
| JP | 2016106697 A | 6/2016 |

OTHER PUBLICATIONS

International Preliminary Report on Patentability from International Application No. PCT/CN2019/096827, dated Jan. 25, 2022, 5 pp.
International Search Report and Written Opinion of International Application No. PCT/CN2019/096827, dated Apr. 17, 2020, 9 pp.
Office Action, and translation thereof, from counterpart Chinese Application No. 202010521811.1 dated Apr. 15, 2025, 16 pp.

* cited by examiner

DEPLOY EMBOLIZATION DEVICE FROM THE DISTAL END OF THE CATHETER INTO TARGET SITE    102

ADJUST POSITION OF EMBOLIZATION DEVICE    104

DETACH EMBOLIZATION DEVICE FROM ELONGATED BODY    106

WITHDRAW ELONGATED BODY FROM VASCULATURE OF THE PATIENT    108

EMBOLIC DEVICE DELIVERY SYSTEM

TECHNICAL FIELD

The disclosure relates to an embolization device.

BACKGROUND

Implantable embolization devices may be used to embolize, e.g., occlude, a vascular site. Possible clinical applications include controlling bleeding from hemorrhages, reducing blood flow to tumors, and treating a diverse number of conditions including, for example, pathologies of the brain, the heart, and the peripheral vascular system. Among other examples, implantable embolization devices may be used to treat aneurysms, vascular malformations, arteriovenous fistulas, pelvic congestion syndrome, and varicoceles. An implantable embolization device may be configured to fill a vascular site in a patient, thereby reducing blood flow, promoting clotting, and eventually occluding the vessel.

SUMMARY

In general, this disclosure describes a system that includes an embolization device and a delivery device configured to deliver the embolization device to a target site within vasculature of a patient. The delivery device includes an elongated body configured to engage an interface member mechanically connected to a proximal portion of the embolization device. The embolization device is attached to the elongated body during delivery of the embolization device to the target site. The elongated body is configured to transmit a pushing force to the embolization device, e.g., to deploy the embolization device from a delivery catheter. The interface member is configured to mate with the elongated body when the embolization device is attached to the elongated body and transmit the pushing force from the elongated body to the embolization device. For example, the interface member or the elongated body may define a protrusion and the other of the interface member or the elongated body may define a recess configured to receive the protrusion. The mating configuration of the interface member and the elongated body may enable better pushability of the embolization device compared to, for example, if the interface member and the elongated body only engaged each other along a flat surface orthogonal to a longitudinal axis of the elongated body.

In some examples, a maximum cross-sectional dimension of the embolization device (while the embolization device is in its delivery configuration) is greater than a maximum cross-sectional dimension of the elongated body, e.g., at the distal portion of the elongated body. The maximum cross-sectional dimension can be, for example, a diameter. The interface member may be configured to provide a transition in maximum cross-sectional dimension between the elongated body and the embolization device to help minimize any adverse impact the difference in maximum cross-sectional dimension between the elongated body and the embolization device may have on the efficient transmission of pushing forces from the elongated body to the embolization device.

This disclosure also describes example methods of using the system.

Clause 1: In some examples, a system comprises an elongated body comprising an elongated body proximal portion and an elongated body distal portion, the elongated body proximal portion having a first maximum cross-sectional dimension; an interface member comprising an interface member proximal portion and an interface member distal portion; and an embolization device configured to expand from a delivery configuration to a deployed configuration. In the delivery configuration, the embolization device comprises a device proximal portion having a second maximum cross-sectional dimension greater than the first maximum cross-sectional dimension. The device proximal portion is mechanically connected to the interface member. The interface member proximal portion is configured to mate with the elongated body distal portion when the embolization device is attached to the elongated body, the interface member having a third maximum cross-sectional dimension greater than the first maximum cross-sectional dimension.

Clause 2: In some examples of the system of clause 1, the elongated body comprises a metal hypotube.

Clause 3: In some examples of the system of clause 1 or 2, the interface member has a minimum cross-sectional dimension less than the second maximum cross-sectional dimension of the device proximal portion of the embolization device.

Clause 4: In some examples of the system of any of clauses 1-3, the device proximal portion is mechanically connected to the interface member distal portion.

Clause 5: In some examples of the system of any of clauses 1-4, the interface member tapers in a proximal direction.

Clause 6: In some examples of the system of any of clauses 1-5, the interface member tapers from a distal portion having a maximum cross-sectional dimension that is substantially equal to the second maximum cross-sectional dimension of the embolization device to a proximal portion having a cross-sectional dimension less than the second maximum cross-sectional dimension of the embolization device.

Clause 7: In some examples of the system of any of clauses 1-6, either the interface member proximal portion or the elongated body distal portion defines a protrusion, and the other of the interface member proximal portion or the elongated body distal portion defines a recess configured to receive the protrusion.

Clause 8: In some examples of the system of any of clause 7, when the interface member proximal portion is mated with the elongated body distal portion, the protrusion and the recess are frictionally engaged and the recess is translatable on the protrusion.

Clause 9: In some examples of the system of clause 7 or 8, the protrusion has at least one shape selected from the group of a frustrum shape, a semi-hemispherical shape, and a pyramidal shape.

Clause 10: In some examples of the system of any of clauses 1-9, the interface member comprises a tapering coil.

Clause 11: In some examples of the system of any of clauses 1-10, the tapering coil defines a constant taper.

Clause 12: In some examples of the system of any of clauses 1-11, the tapering coil defines a stepped taper.

Clause 13: In some examples of the system of clause 12, the tapering coil comprises an inner layer formed by a first section of a wound elongated structure and an outer layer formed by a second section of the wound elongated structure wound partially around the inner layer.

Clause 14: In some examples of the system of any of clauses 1-13, the interface member comprises a plurality of coils having different diameters.

Clause 15: In some examples of the system of clause 14, the plurality of coils comprise a first coil having a first diameter and a second coil having a second diameter greater than the first diameter, the first coil being partially disposed inside the second coil to define a stepped taper of the interface member.

Clause 16: In some examples of the system of any of clauses 1-15, the elongated body defines a first inner lumen and the interface member defines a second inner lumen configured to be aligned with the first inner lumen when the interface member proximal portion is mated with the elongated body distal portion.

Clause 17: In some examples of the system of clause 16, the embolization device is attached to the elongated body by a connecting member extending through the first inner lumen and the second inner lumen, wherein the connecting member is removably attached to the elongated body.

Clause 18: In some examples of the system of any of clauses 1-17, the interface member comprises at least one of platinum, nickel titanium, or stainless steel.

Clause 19: In some examples of the system of any of clauses 1-18, the embolization device is welded to the interface member.

Clause 20: In some examples of the system of any of clauses 1-19, the embolization device defines a proximal opening and the interface member distal portion is configured to be received in the proximal opening to mechanically connect the device proximal portion and the interface member distal portion.

Clause 21: In some examples of the system of any of clauses 1-20, the system further comprises a delivery catheter defining a lumen, wherein the elongated body, the interface member, and the embolization device are configured to be received within the lumen.

Clause 22: In some examples of the system of clause 21, the embolization device is configured to expand radially outward upon deployment from the lumen.

Clause 23: In some examples of the system of clauses 22 or 23, the elongated body is configured to transfer a pushing force to the embolization device to deploy the embolization device from the lumen.

Clause 24: In some examples, a system comprises an elongated body comprising an elongated body proximal portion and an elongated body distal portion; an interface member comprising an interface member proximal portion and an interface member distal portion; and an embolization device comprising a device proximal portion and the device proximal portion mechanically connected to the interface member distal portion. Either the interface member proximal portion or the elongated body distal portion defines a protrusion, and the other of the interface member proximal portion or the elongated body distal portion defines a recess configured to receive the protrusion. The interface member proximal portion is configured to mate with the elongated body distal portion when the embolization device is attached to the elongated body, wherein when the interface member proximal portion mates with the elongated body distal portion, the recess receives the protrusion and a nominal contact area is defined between the protrusion and the recess, and the recess is translatable over three dimensions on the protrusion. The elongated body is configured to transfer a force through some portion of the nominal contact area and through the interface member and to the embolization device.

Clause 25: In some examples of the system of clause 24, the elongated body defines a first inner lumen and the interface member defines a second inner lumen configured to be aligned with the first inner lumen when the interface member proximal portion is mated with the elongated body distal portion, and wherein the embolization device is attached to the elongated body by a connecting member extending through the first inner lumen and the second inner lumen.

Clause 26: In some examples of the system of clauses 24 or 25, the device proximal portion is mechanically connected to the interface member distal portion.

Clause 27: In some examples of the system of any of clauses 24-26, the protrusion has at least one shape selected from the group of a frustrum shape, a semi-hemispherical shape, and a pyramidal shape.

Clause 28: In some examples of the system of any of clauses 24-27, the recess comprises a concave surface surrounding an insertion volume, and when the interface member proximal portion mates with the elongated body distal portion, at least some portion of the protrusion is inserted within the insertion volume.

Clause 29: In some examples of the system of any of clauses 24-28, the embolization device defines a proximal opening and the interface member distal portion is configured to be received in the proximal opening to mechanically connect the device proximal portion and the interface member distal portion.

Clause 30: In some examples of the system of any of clauses 24-29, the system comprises a delivery catheter defining a lumen, wherein the elongated body, the interface member, and the embolization device are configured to be received within the lumen, and wherein the elongated body is configured to transfer a pushing force to the embolization device to deploy the embolization device from the lumen.

Clause 31: In some examples, a method comprises introducing an embolization device system into vasculature of a patient, where the embolization device system comprises an elongated body comprising an elongated body proximal portion and an elongated body distal portion, the elongated body proximal portion having a first maximum cross-sectional dimension, an interface member comprising an interface member proximal portion and an interface member distal portion, and an embolization device configured to expand from a delivery configuration to a deployed configuration. In the delivery configuration, the embolization device comprises a device proximal portion having a second maximum cross-sectional dimension greater than the first maximum cross-sectional dimension, wherein the device proximal portion is mechanically connected to the interface member, and wherein the interface member proximal portion is configured to mate with the elongated body distal portion when the embolization device is attached to the elongated body. The interface member having a third maximum cross-sectional dimension greater than the first maximum cross-sectional dimension. The method further comprises deploying the embolization device at a target site within the vasculature.

Clause 32: In some examples of the method of clause 31, introducing the embolization device system into the vasculature comprises introducing the embolization device system into the vasculature via a delivery catheter.

Clause 33: In some examples of the method of clause 31 or 32, deploying the embolization device at the target site within the vasculature comprises deploying the embolization device from the delivery catheter by at least applying a pushing force to the elongated body proximal portion.

Clause 34: In some examples of the method of any of clauses 31-33, the method further comprises separating the elongated body and the embolization device and withdrawing the elongated body from the vasculature.

The details of one or more examples are set forth in the accompanying drawings and the description below. Other features, objects, and advantages will be apparent from the description and drawings, and from the claims.

DETAILED DESCRIPTION

Figure 1:
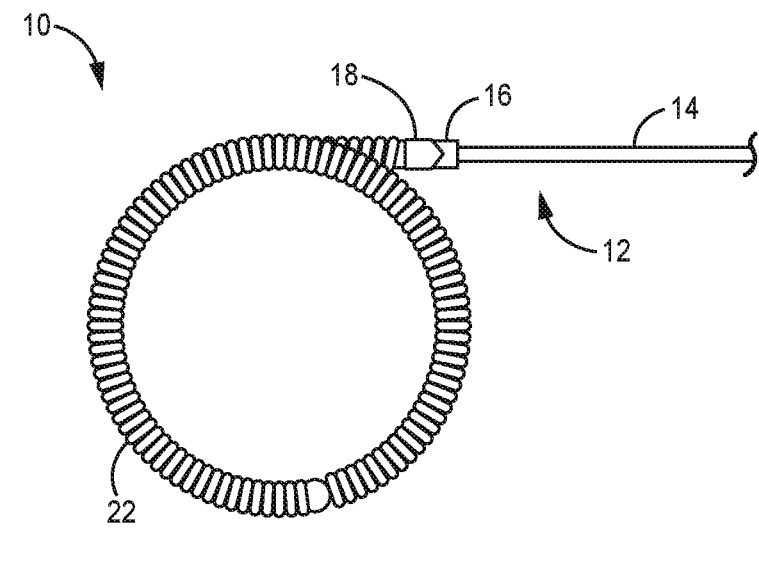
FIG. 1 is a conceptual plan view illustrating an example system including an example embolization device and an example delivery device.

Example medical systems ("system") described herein include an embolization device mechanically connected to an interface member and further attached to an elongated body. The elongated body can be, for example, a delivery device or a part of a delivery device. The interface member is located generally between a distal portion of the elongated body and a proximal portion of the embolization device. In some aspects, a proximal portion of the interface member is configured to mate with a distal portion of the elongated body using, for example, a protrusion-in-recess arrangement, with the recess translatable on the protrusion. Additionally, the embolization device is attached to the elongated body during delivery of the embolization device to a target site within the vasculature of a patient.

The translatable mating arrangement between the elongated body and the interface member in conjunction with the separate attachment between the elongated body and embolization device allows the system to establish a configuration whereby a narrower elongated body can provide a force to a wider embolization device in a variety of directions, with the embolization device remaining attached to the elongated body through the separate attachment. In this manner, the system provides for delivery of the embolization device through, for example, a delivery catheter and further provides for improved manipulability of the embolization device using the elongated body once deployed from the catheter to a target site in a patient. In certain examples the elongated body comprises a positioning element (e.g., a push member) configured to distally advance the embolization device through and out of a lumen of the delivery catheter, and, in some cases, configured to proximally retract the embolization device into the lumen of the delivery catheter.

In some examples the elongated body has a maximum cross-sectional dimension (e.g., a diameter) and the embolization device has a maximum cross-sectional dimension (e.g., a diameter) greater than that of the elongated body. The interface member may be configured to provide a transition in maximum cross-sectional dimension between the elongated body and the embolization device to help minimize any adverse impact the difference in maximum cross-sectional dimension between the elongated body and the embolization device may have on the efficient transmission of pushing forces from the elongated body to the embolization device. For example, the embolization device may be designed to radially expand from a delivery configuration to a deployed configuration once released from the confines of a delivery catheter. With the embolization device in the deployed configuration, the mating between the elongated body distal portion and the interface member proximal portion may provide an ability to more effectively position the embolization device at a target site within vasculature of a patient using the smaller dimensioned elongated body, prior to fully deploying the embolization device by terminating the separate attachment between the embolization device and the elongated body.

To achieve mating between the interface member and the elongated body, either a proximal portion of the interface member ("the interface member proximal portion") or a distal portion of the elongated body ("the elongated body distal portion") may define a protrusion while the other of the interface member proximal portion or elongated body distal portion defines a recess configured to receive the protrusion. The protrusion may have a variety of shapes, including, but not limited to, a frustrum shape, a semi-hemispherical shape, a pyramidal shape, or any shape suitable to be received by a recess. In some aspects and when mated, the protrusion and the recess are frictionally engaged and the recess is translatable on the protrusion. This allows manipulation of the elongated body to adjust the configuration of the mating connection and transfer forces to the embolization device over a variety of differing directions. Additionally, the mating of the elongated body and the interface member may define a nominal contact area between the protrusion and the recess, with the elongated body providing forces to the interface member and embolization device through the nominal contact area.

The embolization device and the elongated body may be attached using any suitable technique. In some examples, a flexible or rigid connecting member provides the concurrent attachment of the embolization device to the elongated body. The connecting member may extend through a first inner lumen of the elongated body and through a second inner lumen of the interface member before attaching to the embolization device. Additionally, the connecting member may attach to an internal member of the embolization device residing within a lumen of the embolization device, to minimize potential interference with the embolization device as the connecting member longitudinally and radially displaces as the elongated body steers the embolization device. The connecting member may be attached in a manner that allows a clinician to facilitate termination of the attachment between the elongated body and the embolization device once the embolization device is positioned within a target site of a patient.

The system described herein may be advanced to a target location (also referred to herein as a target site) within vasculature of a patient in cooperation with a delivery catheter. For example, the system may be configured to slidably translate within an inner lumen of a positioned delivery catheter in response to a pushing force provided through the elongated body by a clinician. As described in further detail below, the mating connection between the elongated body and the interface member operating concurrently with the attachment between the elongated body and the embolization device may allow for effective control of an embolization device having a maximum cross-sectional dimension greater than the elongated body, and may allow for increased manipulability of the embolization device once deployed from the delivery catheter into a target site.

Figure 2:
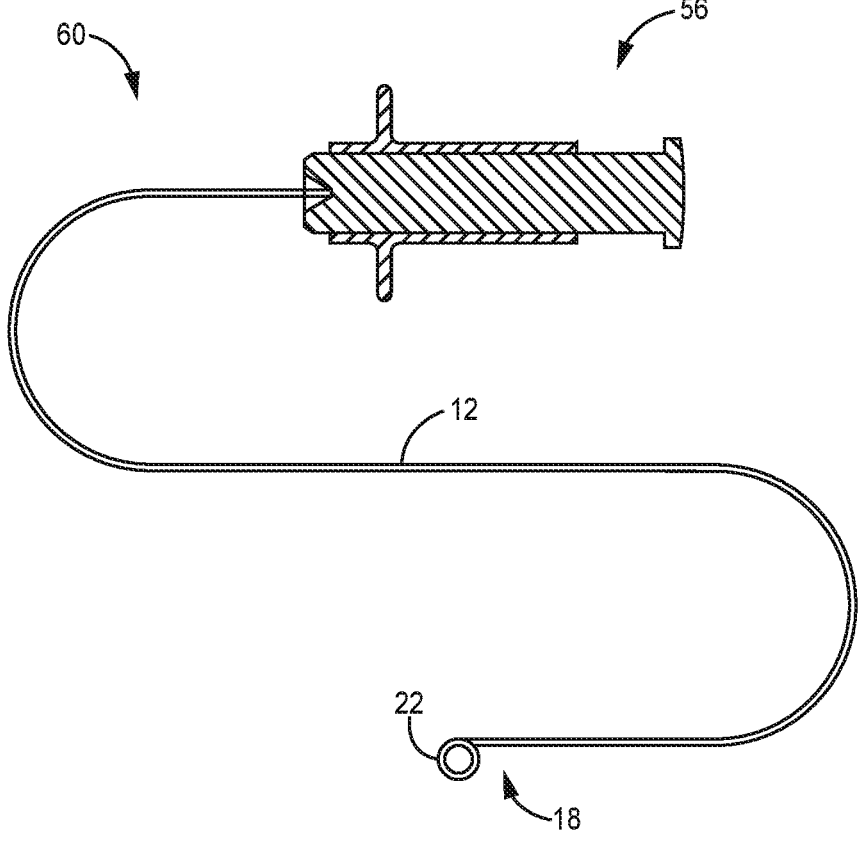
FIG. 2 is a conceptual plan view illustrating an example delivery assembly including the embolization device and the delivery device of FIG. 1 as well as a delivery catheter.

FIG. 1 illustrates an example system 10 comprising an elongated body 12 including an elongated body proximal portion 14 and an elongated body distal portion 16. System 10 further comprises an interface member 18 engaging elongated body distal portion 16 and an embolization device 22 engaging interface member 18. System 10 may be used in an assembly 60 that may include an actuator 56, as illustrated in FIG. 2. A clinician may manipulate the longitudinal position of embolization device 22 relative to a delivery catheter (e.g., catheter 44 shown in FIG. 3) using actuator 56.

Figure 3:
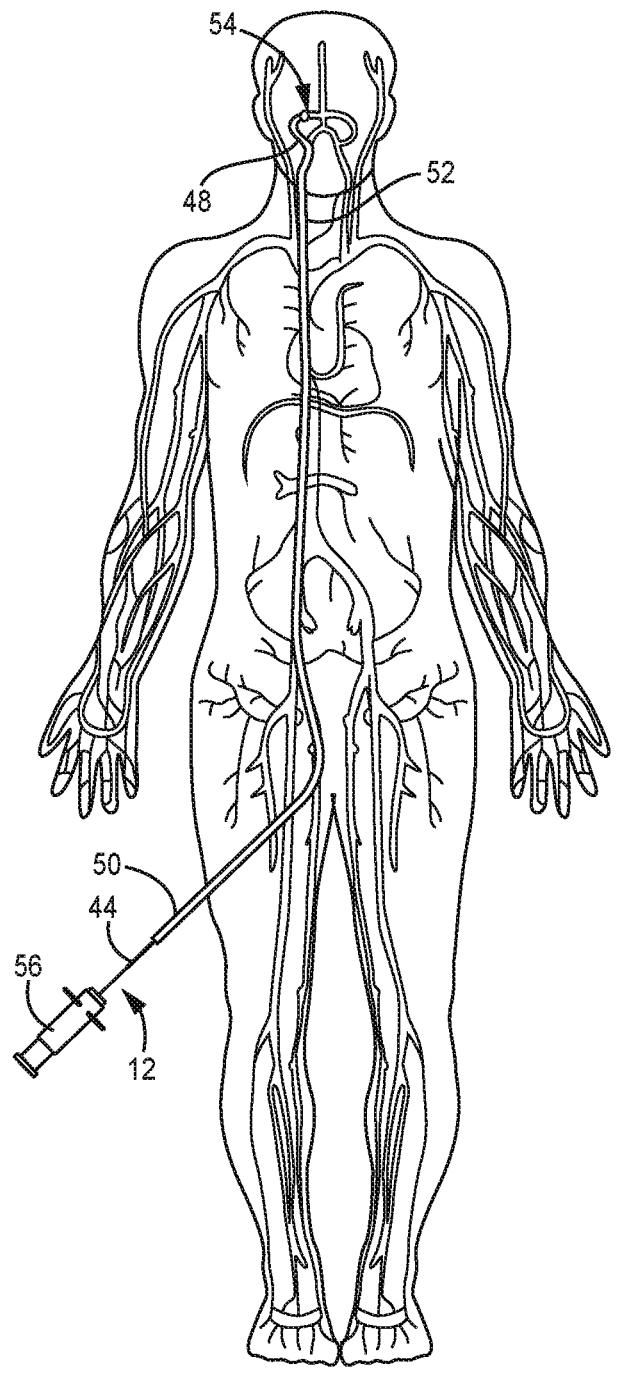
FIG. 3 is a conceptual plan view illustrating the example delivery assembly of FIG. 2 within a human body.

System 10 may be introduced and navigated through vasculature of a patient to a target site within the vasculature using any suitable technique. In some examples, a clinician may use a guide tube 50 (e.g., catheter) to position a catheter 44 in a patient's vasculature, as illustrated in FIG. 3. For example, the clinician may introduce guide tube 50 into the patient's vasculature through an access point such as the groin, e.g., with the aid of a guidewire, and direct distal end 52 of guide tube 50 through the vascular system until it reaches the proximity of a target site 54. The clinician may then introduce catheter 44 into guide tube 50 and advance catheter 44 through guide tube 50 until distal end 48 of catheter 44 exits distal end 52 of guide tube 50 and is positioned near target site 54.

Figure 4:
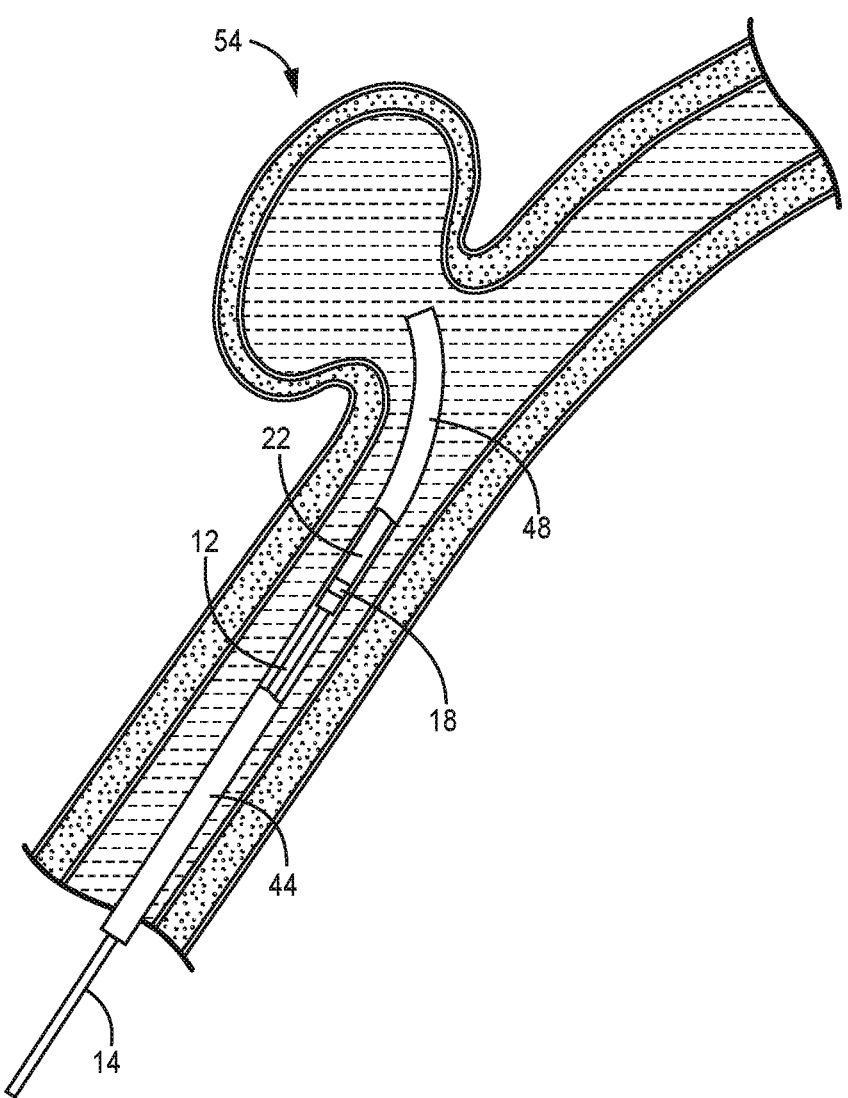
FIG. 4 is conceptual a cross-sectional view of vasculature of a patient and the example delivery assembly of FIG. 2 positioned near a target site within the vasculature.
Figure 5:
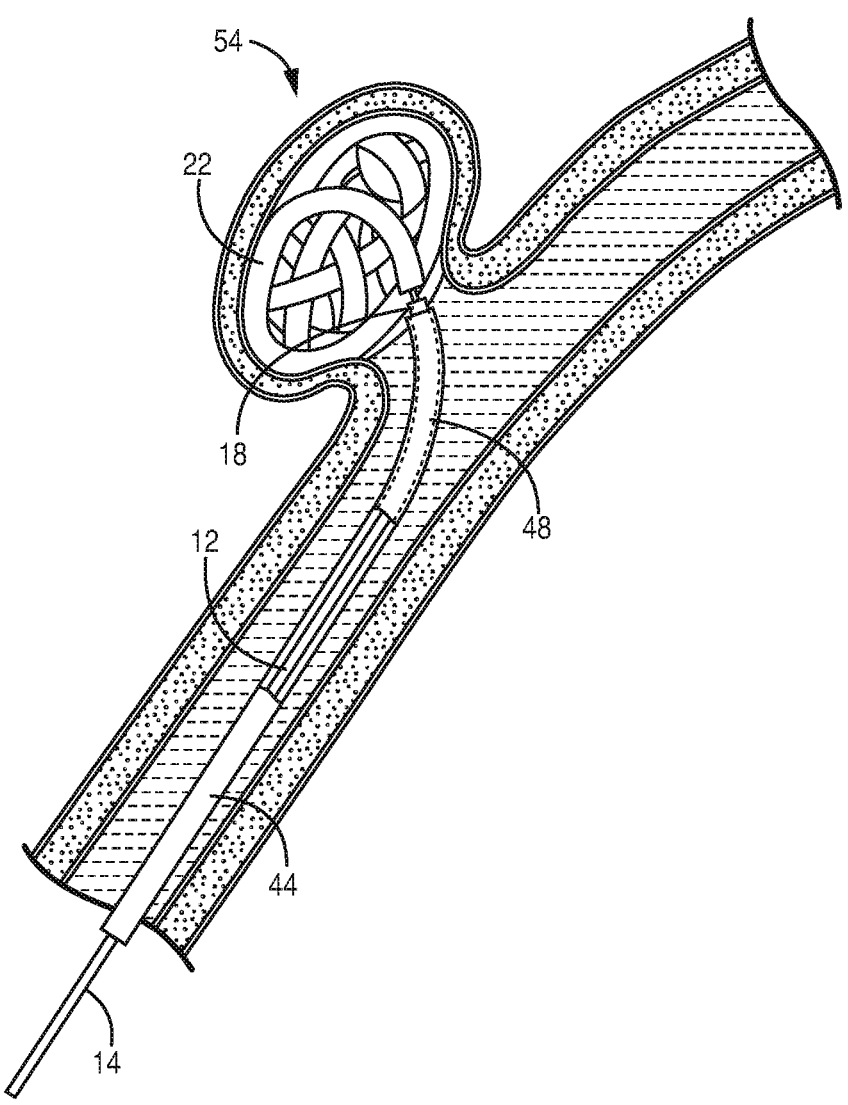
FIG. 5 is conceptual a cross-sectional view of vasculature of the patient and illustrates the embolization device deployed at the target site.

The clinician may deliver embolization device 22 to target site 54 by inserting embolization device 22, interface member 18, and elongated body 12 into catheter 44, and advancing elongated body 12, interface member 18, and embolization device 22 toward distal end 48 of catheter 44 with a pushing force administered to elongated body proximal portion 14. This example mode of implant delivery is illustrated at FIGS. 4 and 5. Embolization device 22 may exhibit differing dimensions depending upon its surrounding environment. This may include a primary dimension when embolization device 22 is in a delivery configuration within a lumen of catheter 44 as embolization device 22 is delivered through catheter 44 and a secondary dimension once embolization device 22 is deployed at target site 54 and in a deployed configuration (shown in FIG. 5). In some examples, embolization device 22 is configured to self-expand from the delivery configuration to the deployed configuration in response to being released from catheter 44. As illustrated at FIG. 5, in its deployed configuration, embolization device 22 may be configured to fill a vascular target site thereby reducing blood flow, promoting clotting, and eventually occluding the vessel. Embolization device 22 can include, for example, a coil, such as, but not limited to, a framing or anchoring coil and/or a packing coil.

Embolization devices have been utilized in this manner for the treatment of hemorrhage, aneurysms, and a multitude of diverse vascular pathologies, including malignancies, vascular malformations, arteriovenous fistulas, pelvic congestion syndrome, and varicoceles. In some cases, relatively large embolic material volumes are required to achieve desirable treatment outcomes. For example, 4-5 meters of coil in total might be used to embolize a 2-3 centimeter (cm) size aneurysm. The delivery systems described herein, which include an elongated body 12 and interface member 18, may facilitate the effective delivery of relatively large dimensioned embolization devices, which may provide for more efficient medical procedures because larger dimensioned embolization devices may reduce the total number of embolization devices required in a specific procedure to achieve the same packing density.

Delivery of relatively large dimensioned embolization devices to target site 54 may present some challenges. For example, delivery of some embolization devices may be accomplished using delivery devices having a relatively small diameter at the distal end (e.g., compared to delivery catheter 44 and/or the relatively large dimensioned embolization devices), in order to maintain the desired softness and pliability for navigating the delivery device through the vasculature of a patient. For larger dimensioned embolization devices, this generates a gap between dimensions—e.g., a gap between the diameter of the delivery device and the diameter of the embolization device. This disruption of the boundary between the delivery device and the embolization device may adversely impact the smoothness by which the embolization device can be advanced and retracted during a procedure, as well as the extent to which the delivery device may be utilized to impart forces to the embolization device in substantially non-longitudinal directions once the embolization device deploys from a delivery catheter. The systems described herein, which include an interface member 18, helps mitigate these challenges by providing a mating connection between the smaller dimensioned delivery devices 12 and larger dimensioned embolization devices 22. The mating connection provides a smooth boundary between differing dimensions to promote more uniform transmission of pushing and retracting forces, and further provides an arrangement whereby non-longitudinal forces may be effectively imparted to the embolization device when manipulation is required for positioning within a target site or other reasons.

Figure 6:
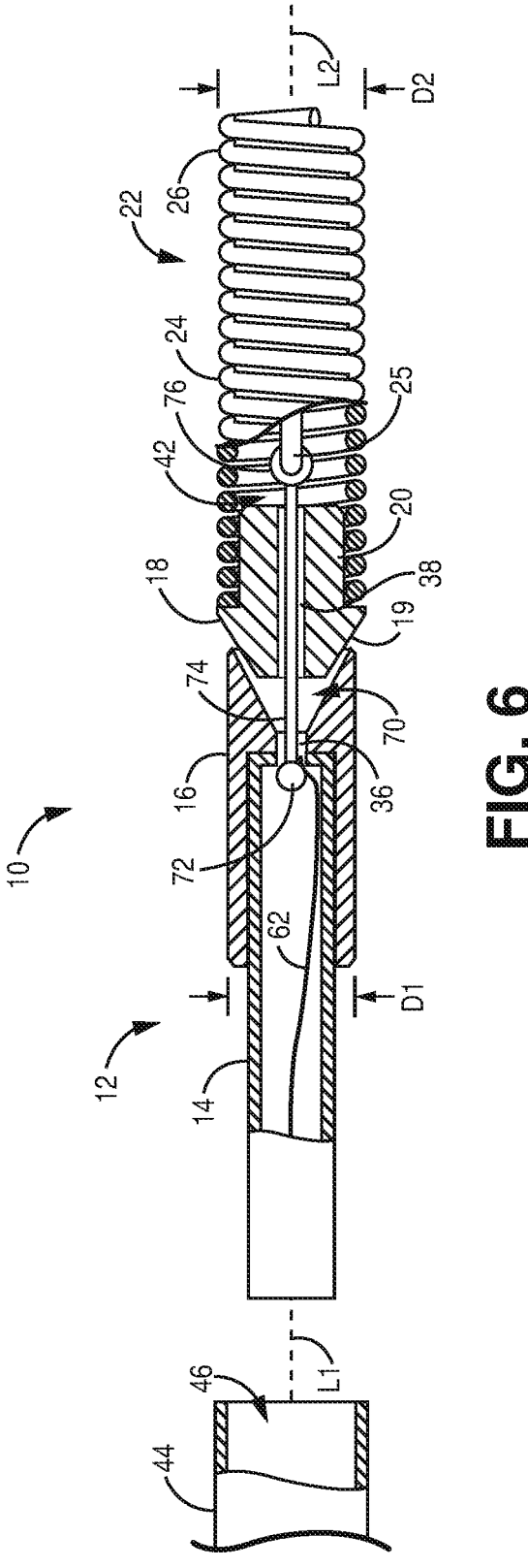
FIG. 6 is a plan view including cross-sectional views and illustrating an example system including an example embolization device and an example delivery device.

FIG. 6 is a side view illustrating an example system 10 including elongated body 12, interface member 18, and embolization device 22, and illustrates in further detail the relationships among elongated body 12, interface member 18, and embolization device 22. Interface member 18 includes an interface member proximal portion 19 and an interface member distal portion 20, and an embolization device 22 includes a device proximal portion 24 and a device distal portion 26. Device proximal portion 24 of embolization device 22 is mechanically connected to interface member 18, e.g., to interface member distal portion 20, and embolization device 22 is further attached to elongated body 12. In the example illustrated at FIG. 6, embolization device 22 is attached to elongated body 12 through a connecting member represented by detach subassembly 70.

Interface member proximal portion 19 is configured to mate with elongated body distal portion 16. In some examples, interface member proximal portion 19 defines a protrusion and elongated body distal portion 16 defines a recess, as illustrated in FIG. 6. In other examples, the interface member proximal portion 19 defines a recess and the elongated body distal portion 16 defines a protrusion. The recess may be configured to receive the protrusion, and interface member proximal portion 19 and elongated body distal portion 16 may mate and form a mating connection when the recess receives the protrusion. In some aspects, the recess is a concave surface surrounding an insertion volume, and when elongated body distal portion 16 mates and forms a mating connection with interface member proximal portion 19, at least some portion of the protrusion is inserted within the insertion volume.

Figure 7:
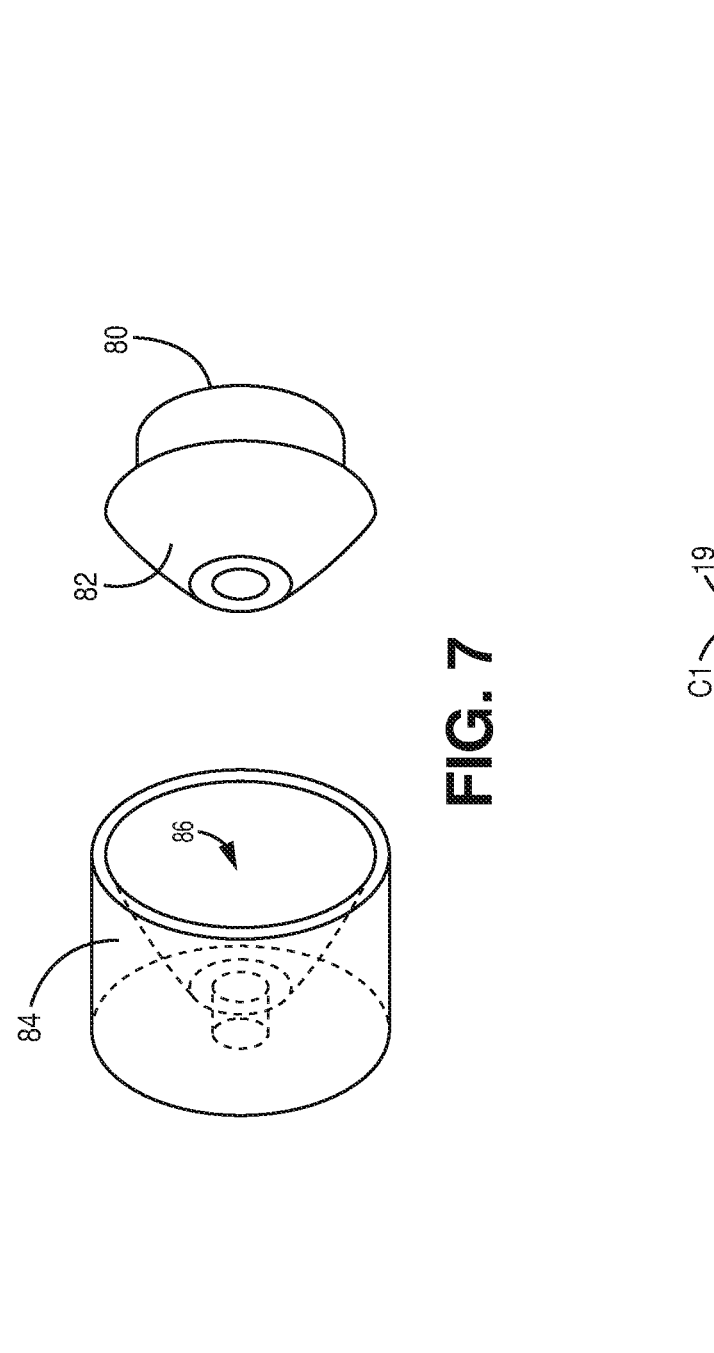
FIG. 7 is an isometric view illustrating an example recess and protrusion.

An example recess and protrusion are shown in FIG. 7. FIG. 7 illustrates isometric renderings of a first component 80 having a protrusion 82 and a second component 84 defining a recess 86, where recess 86 is configured to receive protrusion 82 and provide mating between first component 80 and second component 84. In some examples, first component 80 can be interface member 18 and second component 84 can be elongated body 12, while in other examples, first component 80 can be elongated body 12 and second component 84 can be interface member 18.

In some examples, interface member proximal portion 19 is configured to mate with elongated body distal portion 16 at least when embolization device 22 is attached to elongated body 12. As discussed below, any suitable technique may be used to attach embolization device 22 and elongated body 12. The attachment may provide a clinician with better control over the positioning of embolization device 22 in vasculature of a patient by enabling the clinician to proximally withdraw embolization device 22 (e.g., into or towards delivery catheter 44) during an implant procedure and apply a pushing force to embolization device 22 in multiple directions after device 22 is released from delivery catheter 44.

In certain examples, when interface member proximal portion 19 is mated with elongated body distal portion 16 in a protrusion and recess arrangement, the protrusion and the recess are frictionally engaged and the recess is translatable on the protrusion. This translatability may allow increased manipulability of embolization device 22 once delivered to a target site in a patient. In some cases, effective positioning of embolization device 22 within target site 54 may require a clinician to manipulate elongated body 12 in order to maneuver embolization device 22 into a desired orientation once outside delivery catheter 44 and within target site 54. The mating between elongated body distal portion 16 and interface member proximal portion 19 disclosed herein may aid in the transfer of manipulating forces from the clinician to the embolization device by permitting an enhanced swing angle of the deployed embolization device. This mating may offer advantages over arrangements where pushing elements generate a flat interface with an embolization device. While the flat interface may be useful, limited surface contact on the flat interface when swing angles generate during manipulation of the deployed embolization device can limit embolization device maneuverability.

Figure 8:
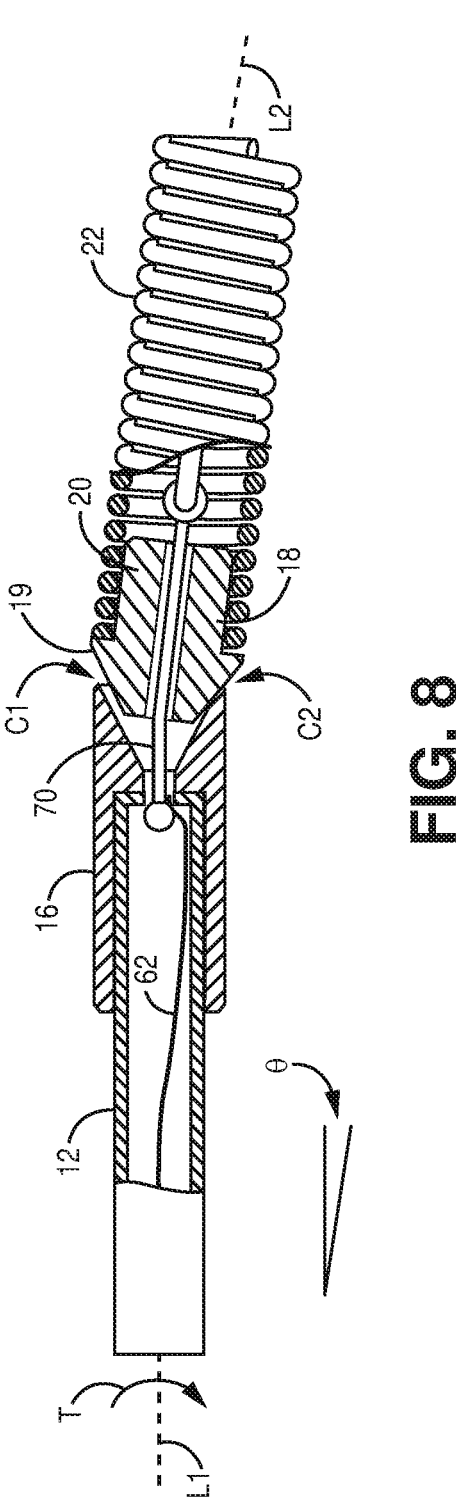
FIG. 8 is a plan view including cross-sectional views and illustrating a configuration of an example system including an example embolization device and an example delivery device.

For example, FIG. 8 depicts elongated body 12 and embolization device 22 in a configuration outside delivery catheter 44, with embolization device 22 experiencing a swing angle relative to elongated body 12, as indicated by the orientation of first longitudinal axis L1 relative to second longitudinal axis L2. The swing angle depicted is approximated by $\ominus$. As indicated, elongated body distal portion 16 defines a recess and interface member proximal portion 19 forms a protrusion. The recess is receiving the protrusion, providing a mating connection between elongated body distal portion 16 and interface member proximal portion 19. Under the orientation described by swing angle $\ominus$, elongated body distal portion 16 and interface member proximal portion 19 establish a nominal contact area which includes the areas generally indicated by C1 and C2.

In examples in which elongated body distal portion 16 and interface member proximal portion 19 have shapes such as first component 80 and second component 84 (FIG. 7), the nominal contact area generated under the orientation of FIG. 8 would extend at least partially and possibly fully around elongated body distal portion 16 and interface member proximal portion 19. This particular nominal contact area, operating at least partially around both first longitudinal axis L1 and second longitudinal axis L2, may enable transmission of a force such as torque T acting on elongated body 12 to be more effectively transmitted to embolization device 22. This effective transmission may be beneficial as a clinician applies varying forces to elongated body 12 during efforts to manipulate embolization device 22 when embolization device 22 is in a deployed condition outside a delivery catheter. In some examples, the recess of the mating connection is translatable over three dimensions on the protrusion, which may enable the clinician to alter the orientation of forces imparted from elongated body 12 to embolization device 22 while maintaining an effective nominal contact area between elongated body distal portion 16 and interface member proximal portion 19.

In some aspects, when elongated body distal portion 16 and interface member proximal portion 19 form a mating connection and second longitudinal axis L2 intersects interface member distal portion 20 and interface member proximal portion 19, a geometric plane intersected by second longitudinal axis L2 defines a cross-sectional area of interface member 18, and a nominal contact area between elongated body distal portion 16 and interface member proximal portion 19 extends at least partially around the perimeter of the cross-sectional area. In some examples, second longitudinal axis L2 extends between a first portion of the nominal contact area and a second portion of the nominal contact area. In some examples, the nominal contact area surrounds the second longitudinal axis L2.

Elongated body proximal portion 14 has a first maximum cross-sectional dimension, which can be, for example, a maximum diameter in examples in which elongated body 23 is circular in cross-section. For example, in the example shown in FIG. 6, elongated body proximal portion 14 has the first maximum cross-sectional dimension indicated by diameter D1. However, the first maximum cross-sectional area may be at any axial location of elongated body proximal portion 14 in other examples. Additionally, embolization device 22 has a second maximum cross-sectional dimension in its delivery configuration, illustrated at FIG. 6 by diameter D2. In some examples, the second maximum cross-sectional dimension is greater than the first maximum cross-sectional dimension of elongated body proximal portion 14.

In some examples, embolization device 22 may have a maximum cross-sectional dimension different from the second maximum cross-sectional dimension and greater than the first maximum cross-sectional dimension of elongated body 12 when embolization device 22 is in its deployed configuration. For example, embolization device 22 may have one maximum cross-sectional dimension when constrained by a surrounding structure such as catheter 44, and another, different maximum cross-sectional dimension when unconstrained. In some examples, embolization device 22 expands radially outward when deployed from a lumen of a delivery catheter, such as catheter 44, e.g., as shown in FIG. 5.

In some examples, elongated body 12 defines a first inner lumen 36 and interface member 18 defines a second inner lumen 38, and second inner lumen 38 is configured to be aligned with first inner lumen 36 when interface member proximal portion 19 is mated with elongated body distal portion 16. In some examples and as depicted at FIG. 6, a first longitudinal axis L1 intersects and extends through elongated body proximal portion 14 and elongated body distal portion 16, and a second longitudinal axis L2 intersects and extends through device proximal portion 24 and device distal portion 26, and second inner lumen 38 is configured to be aligned with first inner lumen 36 when first longitudinal axis L1 is parallel or coincident with second longitudinal axis L2.

During delivery of embolization device 22 to target site 54, device proximal portion 24 of embolization device 22 is mechanically connected to interface member 18. In some examples, the device proximal portion 24 is mechanically connected to the distal portion 20 of interface member 18. In some cases, such as depicted at FIG. 6, device proximal portion 24 forms a proximal opening 42, and interface member distal portion 20 is configured to be received in proximal opening 42. Embolization device 22 may be mechanically connected to interface member 18 by any suitable attachment mechanism. In some examples, device proximal portion 24 is welded to interface member 18.

Additionally, embolization device 22 may be attached to elongated body 12 by any suitable attachment mechanism. In some examples, embolization device 22 is attached to elongated body 12 by a flexible or rigid member attached to embolization device 22 at a first end and elongated body 12 at a second end. The flexible or rigid member may extend through first inner lumen 36 of elongated body 12 and second inner lumen 38 of interface member 18. In some examples, proximal opening 42 of embolization device 22 defines a lumen and embolization device 22 further comprises device internal member 25 residing within the lumen, and the flexible or rigid member is attached to device internal member 25. In some aspects, embolization device 22 is attached to elongated body 12 by detach subassembly 70 comprising ball 72, rod 74, and eyelet 76, with ball 72 attached to elongated body 12 and eyelet 76 attached to embolization device 22. A variety of attachment mechanisms may be used to attach embolization device 22 to elongated body 12, including those described in U.S. Pat. No. 8,328,860, entitled, "IMPLANT INCLUDING A COIL AND A STRETCH-RESISTANT MEMBER," the disclosure of which is hereby incorporated herein by reference in its entirety.

In specific examples, embolization device 22 is removably attached to elongated body 12 such that intentional modification of the attachment by a clinician facilitates a desired separation of elongated body 12 and embolization device 22. Modification of the attachment may be accomplished by a number of mechanisms and methodologies, including but not limited to mechanical detachment, electrolytic detachment, hydraulic detachment, thermal detachment, and others known in the art. In a particular example when detach subassembly 70 attaches embolization device 22 and elongated body 12, a cord 62 may be placed to partially occlude first inner lumen 36 to prevent passage of ball 72, with retraction of cord 62 enlarging the first inner lumen 36 opening sufficiently to allow passage of ball 72 through first inner lumen 36.

Elongated body 12, interface member 18, and embolization device 22 may be formed from any suitable material. In some examples, elongated body 12 comprises a longitudinal member having pliability when under a clinician's control, such as a hypotube. Elongated body 12 may constructed of stainless steel, polymer, or any other suitable material. Interface member 18 may be constructed of any suitable material having good biological compatibility. In some examples, interface member 18 is constructed from one or more of platinum, platinum alloy, nitinol, stainless steel, and other metals. Embolization device 22 may comprise an embolic coil such as, but not limited to, a framing or anchoring coil and/or a packing coil, and may be formed from any suitable biocompatible material. In some examples, embolization device 22 may be a metal or metal alloy, including platinum, a platinum alloy, Nitinol, stainless steel and/or any other metal material characterized as having suitable biocompatibility.

In some examples, system 10 may further comprise a delivery catheter such as catheter 44. Catheter 44 defines a lumen 46, and elongated body 12, interface member 18, and embolization device 22 may be configured to be received within lumen 46. When within lumen 46 of catheter 44, embolization device 22 may be in a delivery configuration. Embolization device 22 may be configured to expand radially outward to its deployed configuration upon deployment from lumen 46, e.g., as shown in FIG. 5. Additionally in this arrangement, elongated body 12 may be configured to transfer a pushing force to embolization device 22 in order to deploy embolization device 22 from lumen 46.

In some examples, the first maximum cross-sectional dimension of elongated body proximal portion 14 is a dimension of a cross-section of elongated body proximal portion 14 residing within a plane perpendicular to first longitudinal axis L1. In some examples, the second maximum cross-sectional dimension of embolization device 22 is a dimension of a cross-section of embolization device 22 residing within a plane perpendicular to second longitudinal axis L2. In some examples the second longitudinal axis L2 intersects and extends through interface member proximal portion 19 and interface member distal portion 20, and a maximum cross-sectional dimension of interface member 18 (referred to herein as a "third" maximum cross-sectional dimension in some examples to distinguish over other maximum cross-sectional dimensions referenced herein) is a dimension of a cross-section of interface member 18 residing within a plane perpendicular to second longitudinal axis L2. In further examples, the minimum cross-sectional dimension of interface member 18 is a dimension of a cross-section of interface member 18 residing within a plane perpendicular to second longitudinal axis L2. Cross-sectional dimension as used herein may refer to a diameter, a width, or an average diameter $D_A$, with $D_A=4A/P$ where A is the area of the cross-section and P is the perimeter of the cross-section.

In some examples interface member 18 tapers in a proximal direction from a cross-sectional dimension substantially equal to a cross-sectional dimension of embolization device 22 to a lesser cross-sectional dimension. The taper may be a constant or a stepped taper. The interface device may comprise a deformable or nondeformable body, and may comprise a wound coil having one or more diameters defining an inner lumen.

In some examples in which interface member 18 tapers in a proximal direction, the profile of interface member 18 may aid in the efficient transmission of pushing forces from a relatively thin elongated body 12 to embolization device 22 when the system 10 is configured for placement within lumen 46 of catheter 44. Interface member 18 may have a minimum cross-sectional dimension less than the second maximum cross-sectional dimension of the device proximal portion 24. Interface member 18 may taper from interface member distal portion 20 having a maximum cross-sectional dimension substantially equal to the second maximum cross-sectional dimension of embolization device 22 to interface member proximal portion 19 having a cross-sectional dimension less than the second maximum cross-sectional dimension of embolization device 22. In some aspects, interface member 18 may taper from interface member distal portion 20 having a maximum cross-sectional dimension less than second maximum cross-sectional dimension of embolization device 22 to interface member proximal portion 19 having a cross-sectional dimension less than the maximum cross-sectional dimension of interface member distal portion 20.

Figure 9A:
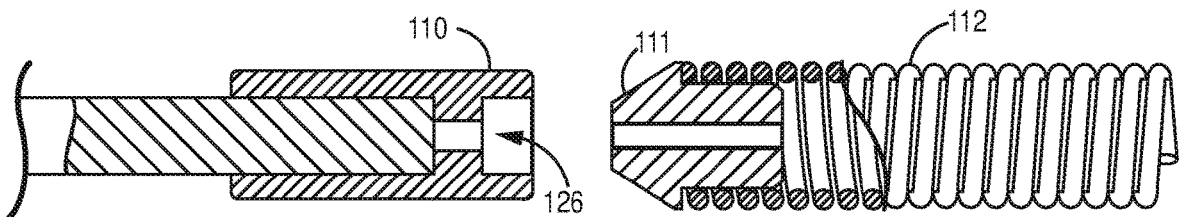
FIG. 9A is a plan view including cross-sectional views illustrating an example embolization device and an example delivery device.
Figure 9B:
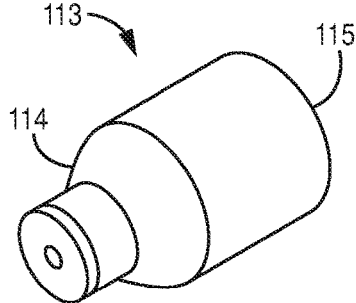
FIG. 9B is an isometric view of an example interface member that may be used with the embolization device and the delivery device of FIG. 9A.

As discussed, a protrusion of a mating connection may have any suitable shape, and a recess of the mating connection may have any shape suitable to receive the protrusion. For example, as illustrated by FIG. 9A, the protrusion and recess may generate substantially rectangular cross-sectional portions. FIG. 9A illustrates elongated body distal portion 110, interface member proximal portion 111, and embolization device 112, with the concave profile of elongated body distal portion 110 configured to receive the substantially rectangular convex profile of interface member proximal portion 111 in recess 126, or vice versa. FIG. 9B illustrates an example interface member 113 employing a frustroconical shape and cylindrical shape which might be employed to generate such a profile of the protrusion. As illustrated, interface member proximal portion 114 provides an example where the cylindrical shape is generally atop the frustroconical shape, with the frustroconical shape between the cylindrical shape and interface member distal portion 115. In examples such as that of FIG. 9B comprised of two or more combined shapes, a first shape and a second shape may have any axial lengths relative to one another or relative to any portion of interface member 113, interface member proximal portion 114, or interface member distal portion 115. In some examples, the axial lengths denote dimensions in a direction parallel to an axis intersecting interface member proximal portion 114 and interface member distal portion 115.

Figure 10A:
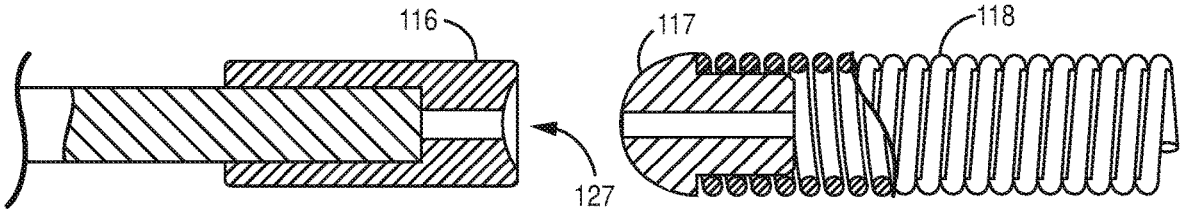
FIG. 10A is a plan view including cross-sectional views illustrating an example embolization device and an example delivery device.
Figure 10B:
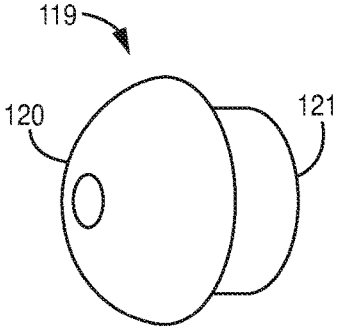
FIG. 10B is an isometric view of an example interface member with the embolization device and the delivery device of FIG. 10A.

In some examples such as illustrated at FIG. 10A, a protrusion and recess may generate substantially semi-circular cross-sectional profiles. FIG. 10A illustrates elongated body distal portion 116, interface member proximal portion 117, and embolization device 118, with the concave profile of elongated body distal portion 116 configured to receive the substantially semi-circular convex profile of interface member proximal portion 117 in recess 127, or vice versa. FIG. 10B illustrates an example interface member 119 with interface member proximal portion 120 employing a semi-hemispherical shape which might be employed to generate such a profile of the protrusion. In examples such as that of FIG. 10B a semi-hemispherical or rounded shape may have any axial length relative to any portion of interface member 119, interface member proximal portion 120, or interface member distal portion 121. The semi-hemispherical or rounded shape may have a constant radius or may have radii which vary along an axial length, and may have any radius relative to any portion of interface member 119, interface member proximal portion 120, or interface member distal portion 121. In some examples, the axial lengths denote dimensions in a direction parallel to an axis intersecting interface member proximal portion 120 and interface member distal portion 121, and radius or radii denote dimensions in a direction generally perpendicular to the axis.

Figure 11A:
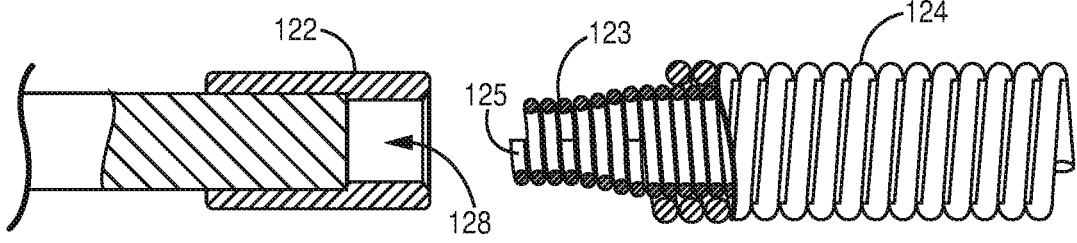
FIG. 11A is a plan view including cross-sectional views illustrating an example embolization device and an example delivery device.
Figure 11B:
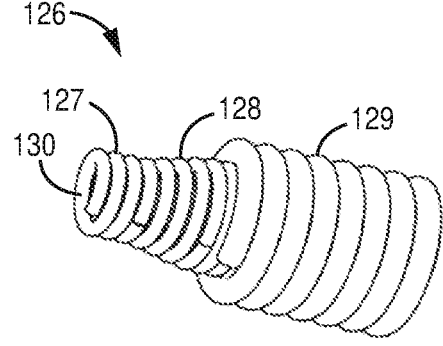
FIG. 11B is an isometric view of an example interface member with the embolization device and the delivery device of FIG. 11A.

In some examples, such as depicted in FIG. 11A, the interface member proximal portion comprises a coil, such as a tapering coil. The tapering coil may define a constant taper in some examples. FIG. 11A illustrates elongated body distal portion 122, interface member proximal portion 123 comprising coil 125, and embolization device 124, with the concave profile of elongated body distal portion 122 configured to receive the convex profile of interface member proximal portion 123 in recess 128, or vice versa. FIG. 11B illustrates an example interface member 126 comprising wound coil 130, with interface member proximal portion 127 defining a shape which might be employed to generate such a profile of the protrusion. In some examples, wound coil 130 comprises interface member distal portion 128 having a first section of would coil 130 mechanically connected to embolization device 129. In some examples, embolization device 129 is wound partially around the first section of wound coil 130. In examples such as that of FIG. 11B, wound coil 130 may define a shape having any axial length relative to interface member 126, interface member proximal portion 127, or interface member distal portion 128. In some examples, wound coil 130 may have a constant radius or may have radii which vary along an axial length, and may have any radius relative to any portion of interface member 126, interface member proximal portion 127, or interface member distal portion 128. In some examples, the axial lengths denote dimensions in a direction parallel to an axis intersecting interface member proximal portion 127 and the interface member distal portion 128, and radius or radii denote dimensions in a direction generally perpendicular to the axis.

Figure 12A:
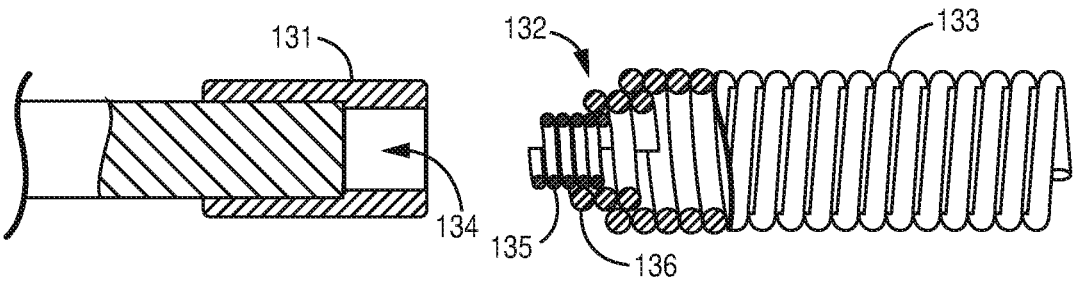
FIG. 12A is a plan view including cross-sectional views illustrating an example embolization device and an example delivery device.
Figure 12B:
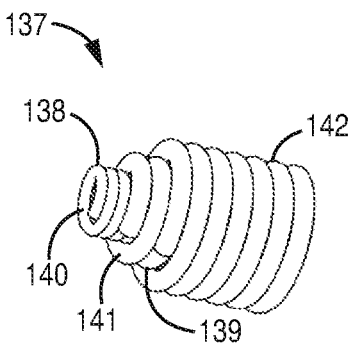
FIG. 12B is an isometric view of an example interface member with the embolization device and the delivery device of FIG. 12A.

In some examples, the tapering coil may also define a stepped coil, as illustrated in FIG. 12A. FIG. 12A illustrates elongated body distal portion 131, interface member proximal portion 132, and embolization device 133, with the concave profile of elongated body distal portion 131 configured to receive the convex profile of interface member proximal portion 132 in recess 134, or vice versa. As illustrated at FIG. 12A, interface member proximal portion 132 may comprise one or more coils such as first coil 135 and second coil 136. FIG. 12B illustrates an example interface member 137 comprising first wound coil 140 and second would coil 141, with interface member proximal portion 138 defining a shape which might be employed to generate such a profile of the protrusion. In some examples, first wound coil 140 comprises an inner layer and second wound coil 141 comprises an outer layer wound partially around the inner layer. In some examples, second wound coil 141 comprises interface member distal portion 139 mechanically connected to embolization device 142. In some examples, embolization device 142 is wound partially around second wound coil 141. In examples such as that of FIG. 12B, a first wound coil and/or a second wound coil may have any axial lengths relative to one another or relative to any portion of interface member 137, interface member proximal portion 138, or interface member distal portion 139. In some examples, the first wound coil and/or the second wound coil may have a constant radius or may have radii which vary along an axial length, and may have any radius relative to any portion of interface member 137, interface member proximal portion 138, or interface member distal portion 139. In some examples, the axial lengths denote dimensions in a direction parallel to an axis intersecting interface member proximal portion 138 and interface member distal portion 139, and radius or radii denote dimensions in a direction generally perpendicular to the axis.

Other arrangements may be envisioned whereby a protrusion of a mating connection has a particular shape, and a recess of the mating connection is configured to receive at least some portion of the particular shape, in order to generate the mating connection.

Figure 13:
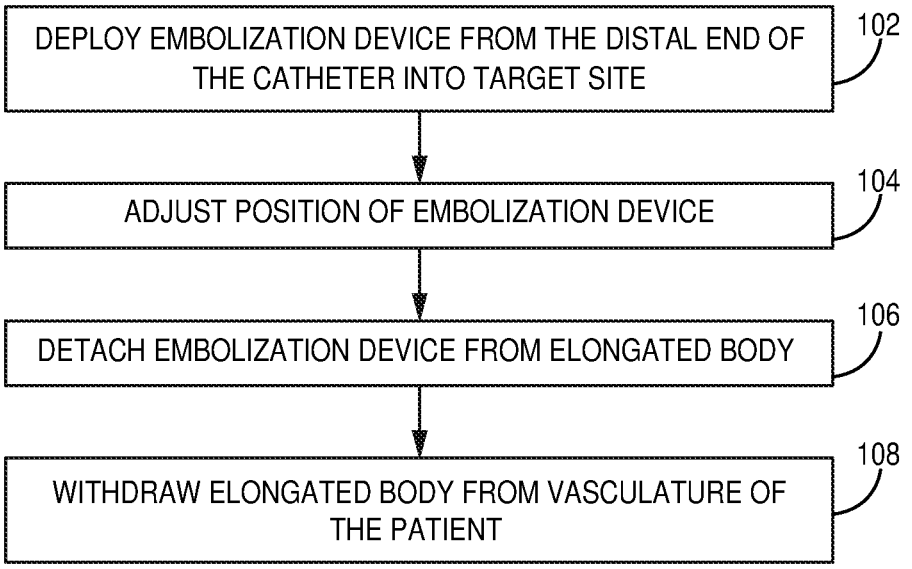
FIG. 13 is a flow diagram illustrating an example method of using an example system.

FIG. 13 is a flow diagram of an example method of using system 10 (FIG. 6). In some examples, embolization device 22, interface member 18, and elongated body 12 are preloaded into lumen 46 of catheter 44 by a distributor of embolization device 22. In other examples, a clinician may introduce embolization device 22, interface member 18, and elongated body 12 into lumen 46 of catheter 44. A clinician may position a distal portion of catheter 44 proximate target site 54 and advance embolization device 22 through lumen 46 to at least partially deploy embolization device 22 at a target site within a patient (102). For example, the clinician may apply a pushing force to elongated body 12 (e.g., to elongated body proximal portion 14), which is transmitted through the mating connection to interface member 18 and embolization device 22. The clinician may continue to advance system 10 toward the distal end of the catheter 44, until device 22 is at least partially deployed from lumen 46 and at target site 54.

In some examples, the clinician may adjust the position of embolization device 22 relative to target site 54 (104). For example, the clinician may manipulate the position of embolization device 22 to position embolization device 22 as desired at target site 54, by maintaining or establishing mating between elongated body distal portion 16 and interface member proximal portion 19, then applying an axial or non-axial force to elongated body proximal portion 14 and transmitting the force from elongated body proximal portion 14 through the mating connection and to interface member 18 and embolization device 22, until the force generates motion of embolization device 22 in the target site 54.

After embolization device 22 is positioned as desired at target site 54, the clinician may detach embolization device 22 from elongated body 12 (106). For example, the clinician may facilitate detachment by retracting cord 62 and allowing ball 72 to pass through first inner lumen 36 (FIG. 6), or by using another appropriate methodology.

After embolization device 22 is detached (and separated) from elongated body 12, the clinician may proximally withdraw elongated body 12 from the vasculature of the patient, e.g., through lumen 46 of catheter 44, while embolization device 22 and interface member 18 remain at target site 54 (108).

Various examples have been described. These and other examples are within the scope of the following claims.

What is claimed is:

1. A system comprising:
an elongated body comprising an elongated body proximal portion and an elongated body distal portion, the elongated body proximal portion having a first maximum cross-sectional dimension, wherein the elongated body distal portion comprises an inner surface defining a first inner lumen, and an outer surface extending more distally than the inner surface;
an interface member comprising an interface member proximal portion and an interface member distal portion;
an embolization device configured to expand from a delivery configuration to a deployed configuration, wherein the interface member distal portion is attached to the embolization device; and
a connecting member configured to contact the embolization device to mechanically connect the embolization device and the elongated body, wherein the connecting member is configured to extend into and out of the first inner lumen to mechanically connect the embolization device and the elongated body,
wherein in the delivery configuration, the embolization device comprises a device proximal portion having a second maximum cross-sectional dimension greater than the first maximum cross-sectional dimension, and
wherein the interface member proximal portion is configured to mate with the elongated body distal portion when the connecting member contacts and mechanically connects the embolization device and the elongated body, the interface member having a third maximum cross-sectional dimension greater than the first maximum cross-sectional dimension wherein the elongated body distal portion comprises a distal-most end, wherein the interface member proximal portion is configured to mate with the distal-most end of the elongated body distal portion, and wherein the distal-most end of the elongated body comprises a minimum cross-sectional dimension greater than the first maximum cross-sectional dimension.

2. The system of claim 1, wherein the interface member has a minimum cross-sectional dimension less than the second maximum cross-sectional dimension of the device proximal portion of the embolization device.

3. The system of claim 1, wherein the interface member tapers from the interface member distal portion having a maximum cross-sectional dimension that is substantially equal to the second maximum cross-sectional dimension of the embolization device to the interface member proximal portion having a cross-sectional dimension less than the second maximum cross-sectional dimension of the embolization device.

4. The system of claim 1, wherein either the interface member proximal portion or the elongated body distal portion defines a protrusion, and the other of the interface member proximal portion or the elongated body distal portion defines a recess configured to receive the protrusion.

5. The system of claim 4, wherein when the interface member proximal portion is mated with the elongated body distal portion, the protrusion and the recess are frictionally engaged and the recess is translatable over three dimensions on the protrusion.

6. The system of claim 4, wherein the protrusion has at least one shape selected from the group of a frustrum shape, a semi-hemispherical shape, and a pyramidal shape.

7. The system of claim 1, wherein the interface member defines a second inner lumen configured to align with the first inner lumen when the interface member proximal portion is mated with the elongated body distal portion, and wherein the connecting member is configured to extend through the first inner lumen and the second inner lumen when the connecting member mechanically connects the embolization device and the elongated body.

8. The system of claim 7, further comprising a cord configured to partially occlude the first inner lumen, wherein the cord is configured to prevent a passage of a ball portion of the connecting member through the first inner lumen when the cord partially occludes the first inner lumen, and wherein the ball portion is configured to pass through the first inner lumen when the cord is retracted from the first inner lumen.

9. The system of claim 1, wherein the embolization device defines a proximal opening and the interface member distal portion is configured to be received in the proximal opening to mechanically connect the device proximal portion and the interface member distal portion.

10. The system of claim 1, further comprising a delivery catheter defining a lumen, wherein the elongated body, the interface member, and the embolization device are configured to be received within the lumen.

11. The system of claim 10, wherein the elongated body is configured to transfer a pushing force to the embolization device to deploy the embolization device from the lumen.

12. The system of claim 1, wherein the connecting member is configured to extend into the embolization device to mechanically connect the embolization device and the elongated body.

13. The system of claim 1, wherein the elongated body distal portion comprises a second inner surface defining a tapered inner lumen, the tapered inner lumen fluidly connected to the first inner lumen and tapering from the distal-most end to the first inner lumen.

14. A system comprising:

an elongated body comprising an elongated body proximal portion and an elongated body distal portion, the elongated body proximal portion having a first maximum cross-sectional dimension, wherein the elongated body distal portion comprises an inner surface defining a first inner lumen, and an outer surface extending more distally than the inner surface;

an interface member comprising an interface member proximal portion and an interface member distal portion;

an embolization device configured to expand from a delivery configuration to a deployed configuration, the embolization device comprising a device proximal portion and the device proximal portion, and the device proximal portion attached to the interface member distal portion; and a connecting member configured to contact the embolization device to mechanically connect the embolization device and the elongated body, wherein the connecting member is configured to extend into and out of the first inner lumen to mechanically connect the embolization device and the elongated body, wherein the interface member distal portion is attached to the embolization device, wherein either the interface member proximal portion or the elongated body distal portion defines a protrusion, and the other of the interface member proximal portion or the elongated body distal portion defines a recess configured to receive the protrusion, wherein the interface member proximal portion is configured to mate with the elongated body distal portion when the recess receives the protrusion and the connecting member contacts and mechanically connects the embolization device and the elongated body, wherein when the recess receives the protrusion, a nominal contact area is defined between the protrusion and the recess and the recess is translatable over three dimensions on the protrusion, wherein the elongated body is configured to transfer a force through some portion of the nominal contact area and through the interface member and to the embolization device, wherein in the delivery configuration, the device proximal portion has a second maximum cross-sectional dimension greater than the first maximum cross-sectional dimension, and wherein the interface member having a third maximum cross-sectional dimension greater than the first maximum cross-sectional dimension wherein the elongated body distal portion comprises a distal-most end, wherein the interface member proximal portion is configured to mate with the distal-most end of the elongated body distal portion, and wherein the distal-most end of the elongated body comprises a minimum cross-sectional dimension greater than the first maximum cross-sectional dimension.

15. The system of claim 14, wherein the interface member defines a second inner lumen configured to be aligned with the first inner lumen when the interface member proximal portion is mated with the elongated body distal portion, and wherein the connecting member extends through the first inner lumen and the second inner lumen.

16. The system of claim 14, wherein the interface member proximal portion defines the protrusion and the elongated body distal portion defines the recess.

17. The system of claim 14, wherein the protrusion has at least one shape selected from the group of a frustrum shape, a semi-hemispherical shape, and a pyramidal shape.

18. A method comprising:

introducing an embolization device system into vasculature of a patient, the embolization device system comprising:

an elongated body comprising an elongated body proximal portion and an elongated body distal portion, the elongated body proximal portion having a first maximum cross-sectional dimension, wherein the elongated body distal portion comprises an inner surface defining a first inner lumen, and an outer surface extending more distally than the inner surface, an interface member comprising an interface member proximal portion and an interface member distal portion, wherein the interface member distal portion is attached to the embolization device, a connecting member configured to contact the embolization device to mechanically connect the embolization device and the elongated body, wherein the connecting member is configured to extend into and out of the first inner lumen to mechanically connect the embolization device and the elongated body, and an embolization device configured to expand from a delivery configuration to a deployed configuration, wherein the interface member distal portion is attached to the embolization device, wherein in the delivery configuration, the embolization device comprises a device proximal portion having a second maximum cross-sectional dimension greater than the first maximum cross-sectional dimension, and wherein the interface member proximal portion is configured to mate with the elongated body distal portion when the connecting member contacts and mechanically connects the embolization device and the elongated body, the interface member having a third maximum cross-sectional dimension greater than the first maximum cross-sectional dimension; and deploying the embolization device at a target site within the vasculature wherein the elongated body distal portion comprises a distal-most end, wherein the interface member proximal portion is configured to mate with the distal-most end of the elongated body distal portion, and wherein the distal-most end of the elongated body comprises a minimum cross-sectional dimension greater than the first maximum cross-sectional dimension.

19. The method of claim 18, wherein deploying the embolization device at the target site within the vasculature comprises deploying the embolization device from a delivery catheter by at least applying a pushing force to the elongated body proximal portion, the method further comprising:

separating the elongated body and the embolization device; and withdrawing the elongated body from the vasculature.

\*   \*   \*   \*   \*